United States Patent [19]

Bouchaudon et al.

[11] 3,978,078
[45] Aug. 31, 1976

[54] PROCESS FOR THE PREPARATION OF AMPICILLIN

[75] Inventors: Jean Bouchaudon, Morsang-sur-Orge; Pierre Le Roy, Thiais; Mayer Naoum Messer, Bievres, all of France

[73] Assignee: Rhone-Poulenc S.A., Paris, France

[22] Filed: Mar. 10, 1975

[21] Appl. No.: 557,095

Related U.S. Application Data

[62] Division of Ser. No. 442,430, Feb. 14, 1974, Pat. No. 3,926,956.

[30] Foreign Application Priority Data

Feb. 16, 1973 France ............................. 73.05667

[52] U.S. Cl. ........................ 260/306.7 C; 260/239.1
[51] Int. Cl.² .................................... C07D 499/80
[58] Field of Search .................. 260/239.1, 306.7 C

[56] References Cited
UNITED STATES PATENTS 3,855,233  12/1974  Dolfini et al. ................ 260/306.7 C

*Primary Examiner*—Gerald A. Schwartz
*Attorney, Agent, or Firm*—Stevens, Davis, Miller & Mosher

[57] ABSTRACT

Ampicillin is prepared by reacting an inorganic or organic base with a new penicillin G derivative of the formula:

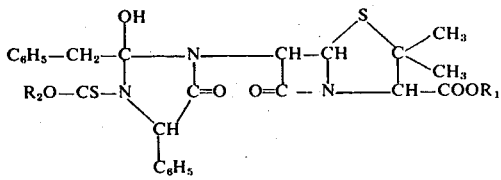

(wherein $R_1$ represents a group protecting the carboxy radical and $R_2$ represents a strong electron-attracting group, e.g. a halogenoethyl group) to open the imidazolidine ring and give an intermediate product of the formula:

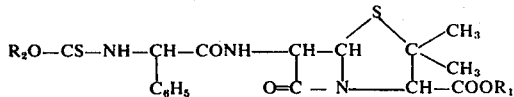

and removing by methods known per se the groups $-R_1$ and $R_2O-CS-$ which protect the carboxy radical and amine functions respectively.

6 Claims, No Drawings

PROCESS FOR THE PREPARATION OF AMPICILLIN

This is a division of application Ser. No. 442,430, filed Feb. 14, 1974, now U.S. Pat. No. 3,926,956.

This invention relates to a new process for the preparation of ampicillin and to new pencillin G derivatives employed in the process.

Ampicillin corresponding to the formula:

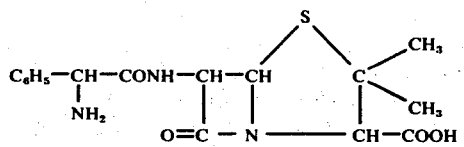

is an antibiotic of outstanding importance due essentially to its wide spectrum of antibiotic activity.

Numerous processes exist for the preparation of ampicillin from 6-aminopenicillanic acid by chemical or enzymatic acylation. In general terms, the chemical methods consist of acylating 6-aminopenicillanic acid by means of a phenylglycine derivative, the amine function of which can be blocked by a protective group, or by means of a phenylacetic acid derivative containing a group which can be converted into an amino radical. After the acylation, the protective group must be removed from the side chain of the intermediate penicillin under conditions which are sufficiently mild to have no effect on the rest of the molecule. These methods are illustrated in, for example, U.S. Pat. No. 2,985,648 (granted to F. P. Doyle et al. on an application filed Feb. 2, 1961) and U.S. Pat. No. 3,079,307 (granted to W. Kaufmann and K. Bauer on an application filed Sept. 18, 1962).

6-Aminopenicillanic acid can be produced from penicillin V in accordance with the process described in U.S. Pat. No. 3,070,511 (granted to G. A. Weitnauer on an application filed Jan. 31, 1961) or from the benzyl ester of penicillin G in accordance with the process described in U.S. Pat. No. 3,107,250 (granted to J. R. Hoover on an application filed Feb. 4, 1960).

It is also known, more particularly from Belgian Pat. No. 763,589 (granted to Toyo Jozo K.K. on an application filed Mar. 1, 1971), to prepare ampicillin from penicillin G, which is an inexpensive and readily available starting material. The process consists essentially of preparing a diacyl derivative of penicillin G of the general formula:

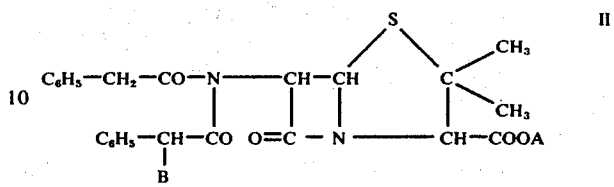

in which A represents a group protecting the carboxy group and B represents a protected amino group, which is thereafter dephenylacetylated, de-esterified and the amine group of which is unblocked.

Because of the similarity in behaviour of the carbonyl functions of the imide group, it is difficult to achieve selective removal of the phenylacetyl group, and so this process leads to mixtures, the separation of the constituents of which is delicate.

It has now been found, and it is this which forms the subject of the present invention, that it is possible to produce ampicillin in good yields from penicillin G derivatives of the general formula:

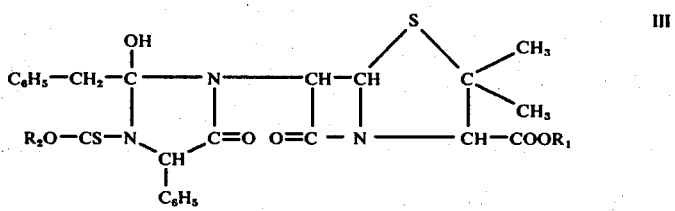

wherein $R_1$ represents a group protecting the carboxy radical and $R_2$ represents a strong electron-attracting group.

The process according to the invention comprises reacting an inorganic or organic base with a penicillin G derivative of general formula III to open the imidazolidine ring and give an intermediate product of the general formula:

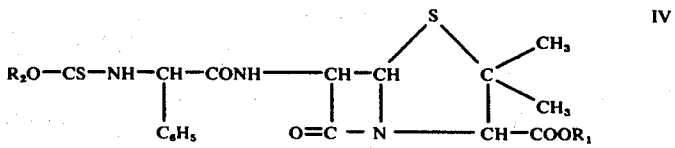

wherein $R_1$ and $R_2$ are as hereinbefore defined, and removing by methods known per se the groups —$R_1$ and $R_2O$—CS— which protect the carboxy radical and amine functions respectively to yield ampicillin.

In general formula III and IV the radicals $R_1$ which protect the carboxy radical during the opening of the imidazolidine ring must be easily removable without affecting the rest of the molecule. Examples of known protective groups are benzyl, p-nitrobenzyl, 2,2,2-trichloroethyl, trityl, dimethylsilyl, trimethylsilyl, phenacyl, p-bromophenacyl, acetyl, propionyl, butyryl, benzoyl, succinyl, methanesulphonyl, p-toluenesulphonyl, methylphosphinyl, methoxyphosphinyl, dimethylphosphinyl, dimethoxyphosphinyl, chloroethoxyphosphinyl, dichloroethoxyphosphinyl, phenylphosphinyl, phenoxyphosphinyl, diphenylphosphinyl, diphenoxyphosphinyl, 4-methyl-1,3,2-dioxaphosphoranyl, 1,3,2-dioxaphosphiranyl and 1,3,2-benzodioxaphospholyl radicals, which can be removed, depending on the particular case, by hydrolysis, hydrogenolysis or acidolysis or by the action of an alkali metal thiophenate.

In the general formulae III and IV the electron-attracting groups $R_2$ are preferably of the formula:

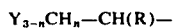    V wherein Y represents a halogen (preferably chlorine) atom, and $n$ is zero, 1 or 2, and R represents a hydrogen atom or the phenyl radical. Advantageously $R_2$ represents the trichloroethyl group.

The treatment of the penicillin G derivatives of general formula III with a base to open the imidazolidine ring and form a compound of general formula IV is carried out in an aqueous, aqueous-organic or organic medium. For example, it is possible to use a mixture of pyridine and water. However, the best results are obtained by using a primary amine, a secondary amine or a dialkylaminoalkylamine which must be selected so that no breaking of the β-lactam bond of the penicillanic ring takes place during the reaction. It is particularly advantageous to use an aliphatic primary amine such as pentylamine or hexylamine, a cycloaliphatic primary amine such as cyclopentylamine or cyclohexylamine, or phenethylamine. 2-Dimethylamino-ethylamine, 3-dimethylamino-propylamine or 3-diethylamino-propylamine may be mentioned amongst the dialkylaminoalkylamines which are very particularly suitable.

The reaction may be carried out in an inert organic solvent such as an aromatic hydrocarbon (e.g. benzene, toluene or the xylenes), an ether (e.g. diethyl ether or tetrahydrofuran), an ester (e.g. ethyl acetate) or a halogenated hydrocarbon (e.g. chloroform).

A suitable reaction temperature is usually between 0° and 25°C.

The group $R_2O$—CS— (wherein $R_2$ is as hereinbefore defined) which proects the amine function of the intermediate product of the general formula IV can be removed under mild conditions which have no effect on the rest of the molecule. Zinc or a zinc alloy in an acid, for example acetic acid, is preferably used.

The group $R_1$ which protects the carboxy radical of the intermediate product of general formula IV can be removed in accordance with the usual methods depending on the group represented by $R_1$.

The groups which protect the amine and carboxy functions of the intermediate products of general formula IV can be removed in any order, and they can even be removed simultaneously, especially when the symbols $R_1$ and $R_2$ represent the same group.

The ampicillin obtained from the intermediate products of general formula IV can, in every case, be isolated from the reaction mixture by methods known per se. By the term "methods known per se" as used in this specification is meant methods heretofore used or described in the chemical literature.

The penicillin G derivatives of general formula III, employed as starting materials in the process of the invention, are new compounds and as such form a further subject of the invention.

According to another feature of the invention, the penicillin G derivatives of general formula III are prepared by the process which comprises reacting a phenylglycine derivative, and more particularly a D-phenylglycine derivative, of the general formula:

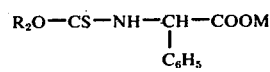    VI wherein $R_2$ is as hereinbefore defined, and M represents an alkali metal atom or an aliphatic or cyclic tertiary ammonium radical in which the alkyl group(s) contain 1 to 4 carbon atoms, such as triethylammonium, N-alkylpiperidinium of N-alkylmorpholinium, with a penicillin G derivative of the general formula:

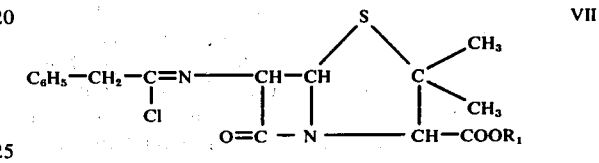    VII wherein $R_1$ is as hereinbefore defined. The reaction is generally carried out in an inert organic solvent, for example acetonitrile, benzene or toluene, or in a mixture of organic solvents, for example a mixture of acetonitrile and benzene, at a temperature between 0° and 30°C.

The phenylglycine derivatives of general formula VI (wherein $R_2$ is of formula V) can be obtained by the reaction of a compound of the general formula:

    VIII (wherein Y, $n$ and R are as hereinbefore defined, and Z represents a chlorine atom or a radical —O—CH(-R)—$CH_nY_{3-n}$ in which Y, $n$ and R are as hereinbefore defined) with a phenylglycine of the general formula:

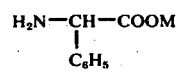    IX wherein M is as hereinbefore defined. The reaction is generally carried out in an inert organic solvent at a temperature between −5° and +25°C.

The compounds of general formula VIII can be obtained, for example, by reacting thiophosgene with an alcohol of the general formula:

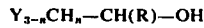    X wherein Y, $n$ and R are as hereinbefore defined.

The penicillin G derivatives of general formula VII can be obtained in accordance with the processes which are described in Belgian Patent No. 763,589.

The following non-limitative Examples illustrate the invention.

EXAMPLE 1

Pyridine (40 cc.) is added to a solution of the trichloroethyl ester of penicillin G (58 g.) in anhydrous benzene (2,250 cc.) kept at 5°C., and then a solution of phosphorus pentachloride (27.5 g.) in anhydrous toluene (600 cc.) is added drop-wise over the course of 2 hours at a temperature of approximately −5° C. The reaction mixture is stirred for 1 hour at a temperature of approximately −5°C. and is then filtered rapidly, and the filtrate is poured into ice-water (600 cc.). The organic phase is isolated and washed successively with an ice-cold saturated solution of sodium chloride (2 × 250 cc.), an ice-cold 5% aqueous solution of sodium bicarbonate (250 cc.) and an ice-cold saturated solution of sodium chloride (250 cc.), and is then dried over magnesium sulphate at 0°C. After filtration, a solution of potassium trichloroethoxythiocarbonyl D-α-phenylglycinate (44 g.) in acetonitrile (450 cc.) is added over the course of a few minutes. The reaction mixture is stirred for a further 16 hours at 20°C. and is then concentrated to dryness under reduced pressure (12 mm Hg) at 30°C. The residue obtained is taken up in benzene (100 cc.). The insoluble matter is filtered off and the filtrate is chromatographed on a column of Merck Kieselgel (500 g.) (0.05 − 0.20 mm., pH neutral) (diameter of the column 6 cm., height 47 cm.), eluting with benzene. 125 cc. fractions are collected. Fractions 8 to 75 are combined and concentrated to dryness under reduced pressure (12 mm.Hg) at 30°C. to give trichloroethyl 6-(2-benzyl-2-hydroxy-5-oxo-4-phenyl-3-trichloroethoxythiocarbonyl-imidazolidin-1-yl)-penicillinate (38 g.).

Rf = 0.76 [silica gel; chloroform/ethyl acetate (85–15 by volume)]

Analysis Calculated % C, 44.07; H, 3.44; N, 5.31; Cl, 26.91; S, 8.11. Found C, 44.2; H, 3.5; N, 5.3; Cl, 26.85; S, 7.95.

Nuclear magnetic resonance spectrum (CDCl$_3$) 1.4 (s, 3H) —CH$_3$; 1.45 (s, 3H) —CH$_3$; 3.25 and 4.55 (AB, J=14, 2H) —CH$_2$— in the 2'-position; 4.1 (s, 1H) —CH— in the 4'-position; 4.4 and 5.1 (AB, J=12, 2H) Cl$_3$CCH$_2$OCS—; 4.55 (s, 1H) H— in the 3-position; 4.7 (AB, J=11, 2H) —CH$_2$— in the 3-position; 5.1 (d, J=4, 1H) H— in the 5-position; 5.5 (d, J=4, 1H) H— in the 6-position; 6.5 (s, 1H) —OH; 7.0 to 7.4 (mt, 10H) —C$_6$H$_5$.

Infra-red spectrum (determination as a solution in bromoform). Its characteristic bands are as follows (expressed in cm$^{-1}$): 1,795, 1,760, 1,745, 1,460 and 815.

Furthermore, fractions 111 to 160 from the aforementioned chromatography are combined and concentrated to dryness under reduced pressure (12 mm.Hg) at 30°C.; the trichloroethyl ester of penicillin G (25.5 g.) is thus recovered.

Trichloroethoxythiocarbonyl-D-α-phenylgylcine can be prepared in accordance with one of the following procedures:

1. A solution of trichloroethyl chlorothioformate (47 g.) in dioxan (200 cc.) and N sodium hydroxide solution (206 cc.) are added separately, drop-wise, over the course of 30 minutes, and keeping the reaction mixture at about 0°C., to D-α-phenylglycine (31 g.) in a mixture of N sodium hydroxide solution (206 cc.) and diethyl ether (200 cc.) cooled to −2°C. Stirring is continued at 20°C. for 5 hours, then distilled water (250 cc.) is added and the mixture obtained is washed with diethyl ether (4 × 250 cc.). The aqueous phase is brought to pH 2 by adding a 10% solution of phosphoric acid and is extracted with ethyl acetate (4 × 200 cc.). The other extracts are dried over sodium sulphate in the presence of decolourising charcoal and are then concentrated to dryness under reduced pressure (12 mm.Hg) at 50°C.

A yellow oil (53 g.) is thus obtained. This oil is taken up in boiling cyclohexane (2 × 500 cc.), and insoluble matter is filtered off. On cooling, a product crystallises from the filtrate and is filtered off and dried under reduced pressure (0.3 mm.Hg) at 20°C.; trichloroethoxythiocarbonyl-D-α-phenylglycine (10.35 g.) is thus obtained. The mother liquors of this product are concentrated to dryness under reduced pressure (12 mm.Hg) at 50°C.; the residue is taken up in methylene chloride (100 cc.) and petroleum ether (400 cc.; boiling point 70°–100°C.) is added slowly; after filtering off the crystals, a second crop of trichloroethoxycarbonyl-D-α-phenylglycine (10.13 g.), melting at 135°–138°C., is obtained.

Analysis Calculated %: C,38.56; H, 2.94; N, 4.09; S, 9.36; Cl, 31.04. Found: C, 38.7; H, 3.25; N, 4.1; S, 8.85; Cl, 30.3.

Optical rotation: $[\alpha]_D^{20} = -137.4°$ ($c = 1$, dimethylformamide).

Trichloroethyl chlorothioformate can be prepared in the following way:

A solution of trichloroethanol (92 g.) in a mixture of pyridine (100 cc.) and benzene (1 liter) is added drop-wise over the course of 2 hours to a solution of thiophosgene (95 cc.) in benzene (2 liters), the temperature being kept at 20°C. The reaction mixture is stirred for 16 hours at 20°C. and decolourising charcoal (15 g.) is then added. The mixture is stirred for 15 minutes and then the insoluble matter is filtered off and washed with benzene (4 × 100 cc.). The filtrate is cooled to 0°C. and then washed with ice-water (2 × 750 cc.). The organic phase is separated, then dried over sodium sulphate and concentrated under reduced pressure (12 mm.Hg) at 40°C. The residue is distilled under reduced pressure (12 mm.Hg). Trichloroethyl chlorothioformate (47 g.) (b.p. 85°C./12 mm.Hg) is thus obtained.

2. A solution of trichloroethyl thiocarbonate (159 g.) in acetonitrile (800 cc.) is added over the course of 5 minutes to a solution of D-α-phenylglycine (70.36 g.) in N sodium hydroxide solution (466 cc.). The reaction mixture is stirred at 20°C. for 16 hours and is then brought to a pH of approximately 10 by adding N sodium hydroxide solution (50 cc.) and water (400 cc.) and is washed with diethyl ether (4 × 600 cc.). The aqueous phase is acidified by adding N hydrochloric acid (510 cc.). An oil separates out and is extracted with diethyl ether (4 × 800 cc.). The combined organic extracts are washed with water (3 × 400 cc.), dried over sodium sulphate, and then concentrated to dryness under reduced pressure (12 mm.Hg) at a temperature below 30°C. A yellow oil (154 g.) is thus obtained and is dissolved in methylene chloride (290 cc.). Petroleum ether (1,100 cc.; boiling point 70°–110°C.) is added very slowly thereto until crystallisation begins, and then more petroleum ether (1,180 cc.; boiling point 70°–110°C.) is added. After stirring for half an hour, the crystals which have appeared are filtered off, washed with petroleum ether (2 × 100 cc.; boiling point 70°–100°C.) and dried under reduced pressure (0.3 mm.Hg) at 20°C. Trichloroethoxythiocarbonyl-D-α-phenylglycine (76 g.), melting at 140°C., is thus obtained. By concentrating the mother liquors of the above product, a second crop (30 g.) is obtained.

Trichloroethyl thiocarbonate can be prepared in the following way:

A solution of trichloroethanol (184 g.) in a mixture of pyridine (200 cc.) and benzene (1 liter) is added drop-wise over the course of 2 hours and at 20°C. to a solution of thiophosgene (95 cc.) in benzene (2 liters). The reaction mixture is stirred for 16 hours at 20°C. and decolourising charcoal (15 g.) is then added. The mixture is stirred for 15 minutes and then the insoluble material is filtered off and washed with benzene (4 × 100 cc.). The filtrate is cooled to 0°C. and is then washed with ice-water (4 × 750 cc.). The organic solution is dried over sodium sulphate and then concentrated under reduced pressure (12 mm.Hg) at 40°C. The residue is distilled in vacuo (12 mm.Hg) to give trichloroethyl thiocarbonate (164 g.), boiling point 150°C./12 mm.Hg is thus obtained.

EXAMPLE 2

A solution of cyclohexylamine (0.297 g.) in benzene (3 cc.) is added to a solution of trichloroethyl 6-(2-benzyl-2-hydroxy-5-oxo-4-phenyl-3-trichloroethoxythiocarbonyl-imidazolidin-1-yl)penicillinate (2.37 g.) [prepared as described in Example 1] in benzene 15 cc.) kept at about 5°C. The reaction mixture is stirred for 1 hour at 5°C. and then for 2 hours at 20°C. The solution obtained is chromatographed on a column of Merck kieselgel (0.05-0.20 mm., pH neutral) (diameter of the column 2 cm., height 53 cm.). Elution is carried out first with benzene (600 cc.); the corresponding eluate is discarded. Elution is then carried out with a mixture of benzene and ethyl acetate (98/2 by volume), collecting 20 cc. fractions; fractions 33 to 90 are combined and concentrated to dryness under reduced pressure (12 mm.Hg) at 30°C. Trichloroethyl 6-[N-(trichloroethoxythiocarbonyl-D-α-phenylglycyl)amino]penicillinate (1.94 g.) is thus obtained. Rf = 0.85 [silica gel; chloroform/ethyl acetate (95/5 by volume)].

Optical rotation: $[\alpha]_D^{20} = +102.3°$ ($c = 1$, dimethylformamide)

Nuclear magnetic resonance spectrum (CDCl$_3$) 1.5 (s, 3H) —CH$_3$; 1.55 (s, 3H) —CH$_3$; 4.45 (s, 1H) H— in the 3-position; 4.7 (s, 2H) —CH$_2$ in the 3-position; 4.98 (AB, J =12, 0.6H) Cl$_3$CCH$_2$OCS— form B; 5.0 (s, 1.4H) Cl$_3$CCH$_2$OCS— form A; 5.3 to 5.8 (mt, 3H) —CHCO—, H— in the 5-position and H— in the 6-position; 6.4 (mt, 1H) —CSNH—; 7.35 (s, 5H) C$_6$H$_5$—; 7.7 (d, 1H) —CONH—.

Infra-red spectrum (determination as a solution in bromoform): The characteristic bands are as follows (expressed in cm$^{-1}$): 1,785, 1,765, 1,695, 1,500, 830 and 805.

Activated zinc (3 g.) [activated zinc (5 g.) is prepared by adding zinc powder (5 g.) to a mixture of pure acetic acid (25 cc.) and water (5 cc.); the mixture is stirred for a few minutes and then the zinc is filtered off and washed with water (5 × 25 cc.), avoiding bringing it to dryness] is added to a solution of trichloroethyl 6-[N-(trichloroethoxythiocarbonyl-D-α-phenylglycyl)amino]penicillinate (1.35 g.) in a mixture of dioxan (50 cc.), acetic acid (10 cc.) and water (5 cc.) cooled to −5°C. The reaction mixture, kept at about −5°C., is stirred for half an hour and then activated zinc (a further 2 g.) is added and stirring of the reaction mixture, kept at −5°C., is continued for 1 hour. The reaction mixture is filtered; the filtrate is acidified to pH 1.5 by adding ice-cold N hydrochloric acid, washed with diethyl ether (3 × 100 cc.), then saturated with sodium chloride and finally extracted with methyl isobutyl ketone (10 × 50 cc.). The organic extracts are dried over sodium sulphate and then concentrated to dryness under reduced pressure (12 mm.Hg) at 20°C. Ampicillin hydrochloride (470 mg.) is thus obtained.

Rf = 0.15 [silica gel; acetone/acetic acid (95/5 by volume)].

Nuclear magnetic resonance spectrum (D$_2$O) 1.35 (s, 6H) —CH$_3$; 4.32 (s, 1H) H— in the 3-position; 5.1 (s, 1H) —CHCO—; 5.4 (s, 2H) H— in the 5-position and H— in the 6-position; 7.4 (s, 5H) C$_6$H$_5$—.

Infra-red spectrum (determination from tablets of a mixture with KBr): the characteristic bands are as follows (expressed in cm$^{-1}$): 1,775, 1,692, 1,620, 1,605, 1,540 and 1,495.

EXAMPLE 3

Activated zinc (5 g.) [prepared as described in Example 2] is added to a solution of trichloroethyl 6-[N-(trichloroethoxythiocarbonyl-D-α-phenylglycyl)amino]penicillinate (1.34 g.) [prepared as described in Example 2] in a mixture of tetrahydrofuran (40 cc.), acetic acid (10 cc.) and water (1 cc.) cooled to 0°C. The reaction mixture, kept at about 0°C., is stirred for quarter of an hour and is then filtered; water (50 cc.) is added to the filtrate and the mixture is extracted with ethyl acetate (3 × 50 cc.). The combined organic extracts are washed with a saturated solution of sodium chloride (2 × 20 cc.), dried over sodium sulphate and concentrated to dryness under reduced pressure (12 mm.Hg) at 20°C. to give 6-[N-(trichloroethoxythiocarbonyl-D-α-phenylglycyl)amino]penicillanic acid.

Rf = 0.74 [silica gel; acetone/acetic acid (95/5 by volume)].

Infra-red spectrum (determination as a solution in bromoform): the characteristic bands are as follows (expressed in cm$^{-1}$): 1,775, 1,720, 1,685, 1,490 and 830.

Activated zinc (3.3 g.) [prepared as described in Example 2] is added to a solution of 6-[N-(trichloroethoxythiocarbonyl-D-α-phenylglycyl)amino]penicillanic acid (1.16 g.) in a mixture of dioxan (50 cc.), acetic acid (20 cc.) and water (10 cc.) cooled to −5°C. The reaction mixture, kept at −5°C., is stirred for half an hour, then activated zinc (1.7 g.) is added and stirring is continued for 1 hour, keeping the temperature at −5°C. The reaction mixture is filtered and the filtrate is acidified to pH 1.5 by adding ice-cold N hydrochloric acid, washed with diethyl ether (4 × 150 cc.), saturated with sodium chloride and extracted with methyl isobutyl ketone (10 × 50 cc.). The combined organic extracts are dried over sodium sulphate and concentrated to dryness under reduced pressure (12 mm.Hg) at 20°C. Ampicillin hydrochloride (260 mg.) is thus obtained.

Rf = 0.15 [silica gel; acetone/acetic acid (95/5 by volume)].

EXAMPLE 4

Pyridine (40 cc.) is added to a solution of the phenacyl ester of penicillin G (56.5 g.) in anhydrous benzene (1 liter) kept at 5°C., and then a solution of phosphorus pentachloride (27.5 g.) in anhydrous toluene (300 cc.) is added drop-wise, over the course of 1 hour 30 minutes, at a temperature of approximately −5°C. The reaction mixture is stirred for 1 hour at a temperature of approximately −5°C. and is then filtered rapidly and the filtrate is poured into ice-water (600 cc.). organic organinc phase is isolated and is washed successively with an ice-cold saturated solution of sodium chloride (2 × 250 cc.), an ice-cold 5% aqueous solution of sodium bicarbonate (250 cc.) and an ice-cold saturated solution of sodium chloride (250 cc.), and is then dried over magnesium sulphate at 0°C. After filtration, a solution of potassium trichloroethoxythiocarbonyl-D-α-phenylglycinate (38.05 g.) [cf. Example 1] in acetonitrile (350 cc.) is added over the course of a few minutes. The reaction mixture is stirred for 16 hours at 20°C. and is then concentrated to dryness under reduced pressure (12 mm.Hg) at 30°C. The residue obtained is taken up in benzene (100 cc.). The insoluble matter is filtered off and the filtrate is chromatographed on a column of Merck Kieselgel (500 g.) (0.05–0.20 mm., pH neutral) (diameter of the column 6 cm., height 37 cm.). Elution is carried out first with benzene (500 cc.); the corresponding eluate is discarded. Elution is then carried out with a mixture of benzene and ethyl acetate (96/4 by volume), collecting 125 cc. fractions; fractions 10 to 60 are combined and concentrated to dryness under reduced pressure (12 mm.Hg) at 30°C. Phenacyl 6-(2-benzyl-2-hydroxy-5-oxo-4-phenyl-3-trichloroethoxythiocarbonyl-imidazolidin-1-yl)penicillinate (35 g.) is thus obtained.

Rf = 0.61 [silica gel; chloroform/ethyl acetate (80/20 by volume)].

Nuclear magnetic resonance spectrum ($CDCl_3$) 1.45 (s, 3H) —$CH_3$; 1.6 (s, 3H) —$CH_3$; 3.3 and 4.5 (AB,J=14, 2H) —$CH_2$— in the 2'-position; 4.1 (s, 1H) —CH— in the 4'-position; 4.35 and 5.05 (AB, J=12, 2H)$Cl_3CCH_2OCS$—; 4.55 (s, 1H) H— in the 3-position; 5.1 (d, J=4, 1H) H— in the 5-position; 5.2 to 5.7 (mt, 3H) H— in the 6-position and —$CH_2$— in the 3-position; 6.45 (s, 1H) —OH; 7.0 to 7.6 (mt, 13H) $C_6H_5$ and aromatic in the β-position to the CO—; 7.6 to 8.0 (mt, 2H) aromatics in the α-position to the —CO—.

Infra-red spectrum (determination as a solution in bromoform): The characteristic bands are as follows (expressed in $cm^{-1}$): 1,790, 1,745, 1,700, 1,460 and 815.

Furthermore, fractions 61 and thereafter from the aforementioned chromatography are combined and concentrated to dryness under reduced pressure (12 mm. Hg) at 30°C.; the phenacyl ester of penicillin G (16 g.) is thereby recovered.

EXAMPLE 5

A solution of cyclohexylamine (0.99 g.) in benzene (10 cc.) is added drop-wise over the course of 30 minutes to a solution of phenacyl 6-(2-benzyl-2-hydroxy-5-oxo-4-phenyl-3-trichloroethoxythiocarbonyl-imidazolidin-1-yl)-penicillinate (7.76 g.) [prepared as described in Example 4] in benzene (150 cc.). The reaction mixture is stirred for two and a half hours at 20°C. and is then washed successively with 10% ice-cold phosphoric acid (50cc.) and ice-water (5 × 50 cc.). The organic phase is dried over sodium sulphate and concentrated to dryness under reduced pressure (12 mm.Hg) at 30°C. The residue is taken up in diethyl ether (100 cc.), the insoluble matter is filtered off and the filtrate is concentrated to dryness under reduced pressure (12 mm.Hg) at 30°C. The residue is taken up in benzene (50 cc.) and the solution thus obtained is chromatographed on a column of Merck Kieselgel (60 g.) (0.05–0.20 mm., neutral pH) (diameter of the column 2.5 cm., height 30 cm.). Elution is first carried out with benzene (2 liters); the corresponding eluate is discarded. Elution is then carried out successively with benzene containing 1% of ethyl acetate (2liters), benzene containing 1.5% of ethyl acetate (2 liters) and benzene containing 2% of ethyl acetate (2 liters), collecting 50 cc. fractions; fractions 32 to 87 are combined and concentrated to dryness under reduced pressure (12 mm.Hg) at 30°C. Phenacyl 6-[N-(trichloroethoxythiocarbonyl-D-α-phenylglycyl)amino]penicillinate (4.4 g.) is thus obtained.

Rf = 0.61 [silica gel; chloroform/ethyl acetate (80/20 by volume)].

Nuclear magnetic resonance spectrum ($CDCl_3$) 1.62 (s, 6H) —$CH_3$; 4.45 (s, 1H) H— in the 3-position; 4.98 (AB, J=12, 0.6H) $Cl_3CCH_2OCS$— form B; 5.0 (s, 1.4H) $Cl_3CCH_2OCS$— form A; 5.3 to 5.8 (mt, 5H) —CHCO—, H— in the 5-position, H— in the 6-position and —$CH_2$— in the 3-position; 6.4 (large peak, 1H) —NHCS—; 7.1 to 7.6 (mt, 9H) aromatics in the β-position to the CO, $C_6H_5$— and —CONH—; 7.6 to 7.9 (mt, 2H) aromatics in the α-position to the —CO—.

Infra-red spectrum (determination as a solution in bromoform): the characteristic bands are as follows (expressed in $cm^{-1}$): 1,785, 1,755, 1,700, 1,495 and 830.

Sodium thiophenolate (0.14 g.) is added to a solution of phenacyl 6-[N-(trichloroethoxythiocarbonyl-D-α-phenylglycyl)amino]penicillinate (0.66 g.) in dimethylformamide (5 cc.) cooled to 10°C. The reaction mixture, kept between 15° and 20°C., is stirred for 4 hours and is then poured into a mixture of water (500 cc.), 80% phosphoric acid (0.2 cc.) and ethyl acetate (100 cc.) cooled to 0°C. The organic phase is separated and washed with a saturated solution of sodium chloride (5 × 25 cc.), dried over sodium sulphate and then poured into petroleum ether (boiling point 45°–60°C.; 600 cc.). The precipitate which appears is filtered off and dried under reduced pressure (0.3 mm.Hg) at 20°C. to give 6-[N-(trichloroethoxythiocarbonyl-D-α-phenylglycyl)amino]-penicillanic acid (124 mg.).

Rf = 0.75 [silica gel; acetone/acetic acid (95/5 by volume)].

When the product obtained is treated under the conditions described in Example 3, it yields ampicillin hydrochloride.

EXAMPLE 6

Pyridine (38.9 cc.) is added to a solution of the benzyl ester of penicillin G (51.2 g.) in a mixture of anhydrous benzene (400 cc.) and anhydrous toluene (200 cc.) kept at −10°C., and then a solution of phosphorous pentachloride (26.2 g.) in anhydrous toluene (350 cc.) is added drop-wise over the course of 40 minutes at a temperature between −10° and −2°C. The reaction mixture is stirred for 1 hour at a temperature of approximately −5°C. and is then poured into ice-water (1,500 cc.). The organic phase is isolated and washed successively with an ice-cold saturated solution of sodium chloride (250 cc.), and ice-cold 5% aqueous solution of sodium bicarbonate (500 cc.) and an ice-cold saturated solution of sodium chloride (250 cc.). The organic phase is dried over magnesium sulphate at 0°C. After filtration, a solution of potassium trichloroethoxythiocarbonyl-D-α-phenylglycinate (41 g.) [cf. Example 1] in acetonitrile (550 cc.) is added over the bromoform): of a few minutes. The reaction mixture is stirred for 16 hours at 20°C. The precipitate which appears is filtered off and the filtrate is concentrated to dryness under reduced pressure (12 mm.Hg) at 30°C. The residue obtained is dissolved in benzene (500 cc.) and chromatographed on a column of Woelm Kieselgel (500 g.) (0.05–0.20 mm. — neutral pH) (diameter of the column 6 cm., height 35 cm.). Elution is carried out first of all with benzene (500 cc.); the corresponding eluate is discarded. Elution is then carried out with a mixture of benzene and ethyl acetate (96/4 by volume), collecting 100 cc. fractions; fractions 10 to 43 are combined and concentrated to dryness under reduced pressure (12 mm.Hg) at 30°C. Benzyl 6-(2-benzyl-2-hydroxy-5-oxo-4-phenyl-3-trichloroethoxythiocarbonyl-imidazolidin-1-yl)penicillinate (53.2 g.) is thus obtained.

Rf = 0.80 [silica gel; chloroform/ethyl acetate (85/15 by volume)].

Analysis: Calculated %: C, 54.52; H, 4.28; N, 5.61; S, 8.57; Cl, 14.20. Found: C, 54.6; H, 4.55; N, 5.65; S, 8,75; Cl, 14.10.

Nuclear magnetic resonance spectrum (CDCl$_3$) 1.42 (s, 6H) —CH$_3$; 3.3 and 4.5 (AB, J = 14, 2H) —CH$_2$— in the 2'-position; 4.1 (s, 1H) —CH— in the 4'-position; 4.45 (s, 1H) H— in the 3-position; 4.38 and 5.05 (AB, J=12, 2H) Cl$_3$CCH$_2$OCS—; 5.1 (s, 2H) —CH$_2$— in the 3-position; 5.1 (d, J=4, 1H) H— in the 5-position; 5.5 (d, J=4, 1H) H— in the 6-position; 6.45 (s, 1H) —OH; 7.0 to 7.4 (mt, 15H) —C$_6$H$_5$.

Infra-red spectrum (determination as a solution in bromoform): the characteristic bands are as follows (expressed in cm$^{-1}$): 1,790, 1,740, 1,455 and 815.

EXAMPLE 7

A solution of cyclohexylamine (0.99 g.) in benzene (10 cc.) is added to a solution of benzyl 6-(2-benzyl-2-hydroxy-5-oxo-4-phenyl-3-trichloroethoxy-thiocarbonyl-imidazolidin-1-yl)-penicillinate (7.48 g.) [prepared as described in Example 6] in benzene (150 cc.) kept at 20°C. The reaction mixture is stirred for 2 hours 30 minutes at 20°C., and then the solution obtained is chromatographed on a column of Merck Kieselgel (0.05–0.20 mm., neutral pH) (diameter of the column 5 cm., height 25 cm.), eluting with a mixture of benzene and ethyl acetate (98/2 by volume) and collecting 120 cc. fractions. Fractions 13 to 64 are combined and concentrated to dryness under reduced pressure (12 mm.Hg) at 30°C. Benzyl 6-[N-(trichloroethoxythiocarbonyl-D-α-phenylglycyl)amino]penicillinate (5.7 g.) is thus obtained.

Rf = 0.77 [silica gel; chloroform/ethyl acetate (85/15 by volume)].

Analysis: Calculated %: C, 49.49; H, 4.15; N, 6.66; S, 10.16; Cl, 16.85. Found: C, 49.85; H, 4.15; N, 6.25; S, 9.5; Cl, 15.9.

Optical rotation: $[\alpha]_D^{20} = +131.3°$ (c = 1.4, dimethylformamide)

Nuclear magnetic resonance spectrum (CDCl$_3$) 1.35 (s, 3H) —CH$_3$; 1.45 (s, 3H) —CH$_3$; 4.38 (s, 1H) H— in the 3-position; 4.98 (AB, J=12, 0.6H) Cl$_3$CCH$_2$OCS— form B; 5.0 (s, 1.4H) Cl$_3$CCH$_2$OCS— form A; 5.2 to 5.8 (mt, 3H) —CHCO—, H— in the 5-position and H— in the 6-position; 6.3 (large peak, 1H) —CSNH—; 7.1 to 7.4 (mt, 10H) C$_6$H$_5$—; 7.65 (d, 0H) —CONH—.

Infra-red spectrum determination as a solution in bromoform): the characteristic bands are as follows (expressed in cm$^{-1}$): 1,775, 1,740, 1,690, 1,490 and 825.

A mixture of distilled water (15 cc.), sodium acetate (4 g.) and pure acetic acid (10 cc.) is added to a solution of benzyl 6-[N-(trichloroethoxythiocarbonyl-D-α-phenylglycyl) amino]penicillinate (2.53 g.) in dioxan (40 cc.). The reaction mixture is cooled to 0°C. and activated zinc (12 g.) [prepared as described in Example 2] is added over the course of 2 minutes; the reaction mixture is stirred for half an hour, keeping the temperature at about 0°C. Ice-water (250 cc.) is added to the filtrate which is obtained after filtration; the aqueous phase is washed with ethyl acetate (4 × 100 cc.). The combined organic extracts are washed successively with a 5% aqueous solution of sodium bicarbonate (2 × 50 cc.) and a saturated solution of sodium chloride (2 × 50 cc.), dried over magnesium sulphate and concentrated to dryness under reduced pressure (12 mm.Hg) at 30°C. The residue obtained is taken up in 1% acetic acid (100 cc.), the mixture is stirred for 1 hour 30 minutes, the insoluble matter is filtered off and then a 5% aqueous solution of sodium bicarbonate (25 cc.) is added to the filtrate and the mixture is extracted with diethyl ether (4 × 100 cc.). The combined ether extracts are dried over magnesium sulphate. The filtrate is concentrated to dryness under reduced pressure (12 mm.Hg) at 30°C. to give benzyl 6-[N-(D-α-phenylglycyl)amino]penicillinate (875 mg.).

Analysis: Calculated %: C, 62.85; H,5.73;N,9.56;S,7.30. Found: C,62.95;H,6.05;N,9.55;S,7.0.

Optical rotation: $[\alpha]_D^{20} = +122.6°$ (c = 1, dimethylformamide)

Nuclear magnetic resonance spectrum (CDCl$_3$) 1.4 (s, 3H) —CH$_3$; 1.6 (s, 3H) —CH$_3$; 1.74 (s wide, 2H) —NH$_2$; 4.4 (s, 1H) H— in the 3-position; 4.5 (s, 1H) —CH—CO—; 5.1 (s, 2H) —CH$_2$— in the 3-position; 5.45 (s, 1H) H— in the 5-position; 5.5 (dd, J=4, 1H) H— in the 6-position; 7.3 (s, 10H) C$_6$H$_5$—; 7.8 (large peak, 1H) —CONH—.

Infra-red spectrum (determination as a solution in bromoform: The characteristic bands are as follows (expressed in cm$^{-1}$): 1,780, 1,740, 1,680 and 1,495.

EXAMPLE 8

Phosgene (4.4 g.) is added over the course of 50 minutes to a solution of dimethylformamide (3.4 cc.) in benzene (230 cc.) at 30°C. At the end of adding the phosgene, vigorous stirring is maintained for 15 minutes, and then a rapid stream of nitrogen is passed so as to remove the unconverted phosgene. Pyridine (1.6 cc.) followed by the trichloroethyl ester of penicillin G (4.65 g.) dissolved in methylene chloride (10 cc.) are then added to the white suspension thus obtained, which is kept at 30°C. The mixture is stirred for 5 hours. After rapid filtration over clarcel, the filtrate is washed twice with a cold saturated aqueous solution of sodium chloride (total 4 cc.), then once with a 5% ice-cold aqueous solution of sodium bicarbonate (25 cc.) and finally again twice with the sodium chloride solution (total 50 cc.). The filtrate is dried over sodium sulphate and then run into a solution of trichloroethoxythiocarbonyl-D-α-phenylglycine (3.42 g.) [cf. Example 1] in acetonitrile (20 cc.), which has been previously treated with anhydrous triethylamine (1.4 cc.). The mixture is allowed to react for 15 hours, triethylammonium chloride is filtered off and the filtrate is chromatographed on Merck silica (75 g.) (0.05–0.20 mm., neutral pH). Trichloroethyl 6-(2-benzyl-2-hydroxy-5-oxo-4-phenyl-3-trichloroethoxythiocarbonyl-imidazolidin-1-yl)-penicillinate (5.4 g.) is thus obtained.

EXAMPLE 9

A solution of the trichloroethyl ester of penicillin G (1.87 g.) and anhydrous pyridine (0.7 cc.) in toluene (72 cc.) and benzene (4 cc.) is run, with stirring, over the course of 50 minutes, at 24°C., into a suspension of dimethylformamide-thionyl chloride complex (2.05 g.) in benzene (15 cc.). The mixture is stirred for 24 hours. A brown suspension is obtained. The mixture is cooled to about 3°C. and is washed, after decanting, successively with ice-cold solutions of saturated sodium chloride (twice with a total of 20 cc.), then with 5% sodium bicarbonate solution (once with 10 cc.) and finally with saturated sodium chloride solution (twice with a total of 20 cc.). The organic phase is dried over sodium sulphate. After filtration, a solution of potassium trichloroethoxythiocarbonyl-D-α-phenylglycinate (1.52 g.) [cf. Example 1] in acetonitrile (12 cc.) is added rapidly to it, at about 20°C. The mixture is stirred for 15 hours at approximately 20°C. and is then concentrated to dryness under reduced pressure at 30°C. The residue obtained is taken up in benzene (5 cc.). The solution obtained is chromatographed on a column of Merck Kieselgel (48 g.) (0.05–0.20 mm., neutral pH) (diameter of the column 2 cm., height 31 cm.), eluting with a mixture of benzene and ethyl acetate (99/1 by volume). After concentrating the eluates, trichloroethyl 6-(2-benzyl-2-hydroxy-5-oxo-4-phenyl-3-trichloroethoxythiocarbonyl-imidazolidin-1-yl)penicillinate (2.35 g.) is obtained.

The dimethylformamide-thionyl chloride complex used can be prepared in the following way:

A solution of (freshly distilled) thionyl chloride (1.9 cc.) in anhydrous benzene (5 cc.) is added over the course of 15 minutes in the absence of moisture and at approximately 20°C. to a mixture of dimethylformamide (1.8 cc.) and benzene (20 cc.). After stirring for 30 minutes at approximately 20°C., the mixture is concentrated to dryness under reduced pressure (3 mm.Hg); the residue obtained is taken up in benzene (20 cc.) and the mixture is again concentrated to dryness under reduced pressure; this operation is then repeated a further two times. The residue finally obtained is washed by decanting 5 times with benzene (total 100 cc.) and the precipitate finally obtained is dried under reduced pressure.

We claim:

1. A penicillin G derivative of the formula:

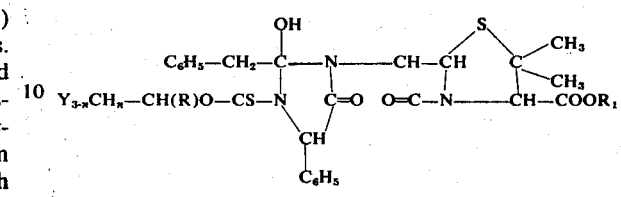

wherein $R_1$ is a group selected from the class consisting of benzyl, p-nitrobenzyl, 2,2,2-trichloroethyl, trityl, dimethylsilyl, trimethylsilyl, phenacyl, p-bromophenacyl, acetyl, propionyl, butyryl, benzoyl, succinyl, methanesulphonyl, p-toluenesulphonyl, methylphosphinyl, methoxyphosphinyl, dimethylphosphinyl, dimethoxyphosphinyl, chloroethoxyphosphinyl, dichloroethoxyphosphinyl, phenylphosphinyl, phenoxyphosphinyl, diphenylphosphinyl, diphenoxyphosphinyl, 4-methyl-1,3,2-dioxaphosphoranyl, 1,3,2-dioxaphosphiranyl and 1,3,2-benzodioxaphospholyl, Y is halogen, $n$ is zero, 1 or 2, and R is hydrogen or phenyl.

2. A penicillin G derivative according to claim 1 wherein Y is chlorine, $n$ is zero and R is hydrogen.

3. A penicillin G derivative according to claim 1 wherein Y is chlorine.

4. A penicillin derivative according to claim 1 which is trichloroethyl 6-(2-benzyl-2-hydroxy-5-oxo-4-phenyl-3-trichloroethoxythiocarbonyl-imidazolidin-1-yl)penicillinate.

5. A penicillin derivative according to claim 1 which is phenacyl 6-(2-benzyl-2-hydroxy-5-oxo-4-phenyl-3-trichloroethoxythiocarbonyl-imidazolidin-1-yl)penicillinate.

6. A penicillin derivative according to claim 1 which is benzyl 6-(2-benzyl-2-hydroxy-5-oxo-4-phenyl-3-trichloroethoxythiocarbonyl-imidazolidin-1-yl)penicillinate.

* * * * *